`US005234682A`

United States Patent [19]
Macchio et al.

[11] Patent Number: 5,234,682
[45] Date of Patent: Aug. 10, 1993

[54] COSMETIC COMPOSITIONS

[75] Inventors: Ralph A. Macchio, Monsey, N.Y.; Julio G. Russ, West Field, N.J.; Salvatore J. Barone, Staten Island, N.Y.

[73] Assignee: Revlon Consumer Products Corporation, New York, N.Y.

[21] Appl. No.: 944,757

[22] Filed: Sep. 14, 1992

Related U.S. Application Data

[63] Continuation of Ser. No. 705,402, May 24, 1991, abandoned, which is a continuation of Ser. No. 541,700, Jun. 21, 1990, abandoned.

[51] Int. Cl.⁵ ..................... A61K 7/035; A61K 7/021
[52] U.S. Cl. ......................... 424/69; 424/63; 424/489; 424/502; 424/78.03
[58] Field of Search ............... 424/63, 69, 78.03, 489, 424/502

[56] References Cited

U.S. PATENT DOCUMENTS

| 4,246,257 | 1/1981 | Elliot et al. ................. 424/69 X |
| 4,309,411 | 1/1982 | Toida et al. ............... 424/78.03 X |
| 4,578,266 | 3/1986 | Tietjen et al. ................ 424/63 |
| 4,837,011 | 6/1989 | Macchio et al. ............... 424/69 |
| 4,988,503 | 1/1991 | Macchio et al. ............... 424/63 |
| 5,023,075 | 6/1991 | Macchio et al. ............... 424/63 |
| 5,030,446 | 7/1991 | Russ et al. .................... 424/63 |

FOREIGN PATENT DOCUMENTS 0095395 5/1985 Japan.

Primary Examiner—Thurman K. Page
Assistant Examiner—S. Gardner
Attorney, Agent, or Firm—Julie Blackburn

[57] ABSTRACT

A cosmetic facial makeup composition comprising spherical silica, particulate nylon, spherical powder, light oils, and cosmetic waxes.

3 Claims, No Drawings

COSMETIC COMPOSITIONS

This is a continuation of copending application Ser. No. 07/705,402, filed May 24, 1991, now abandoned, which in turn is a continuation of 07/541,700, filed Jun. 21, 1990, now abandoned.

TECHNICAL FIELD

The invention is directed to cosmetic compositions useful as foundation, blush, lipstick, eyeshadow, or for other cosmetic uses.

BACKGROUND OF THE INVENTION

Cosmetic compositions for the face such as make up, eyelid shadow or liner, cheek rouge, concealers or cover formulations, lipsticks and the like improve facial aesthetics by imparting more relief to the face, eyes, or lips and by adding moisture or color of the consumer's choice.

Cosmetic makeup compositions intended to apply coatings and/or colors to skin generally fall into one of three categories, namely dry powders; anhydrous fatty systems; or emulsions of the oil in water type.

Dry powders are usually in loose, cake, or compact form. The function of powder is to impart a smooth finish to facial skin, masking minor visible imperfections and shine.

Anhydrous fatty systems such as oils and waxes are in solid, paste, or liquid form. Generally dry powders and anhydrous fatty systems Provide no moisture to the skin.

On the other hand, oil in water emulsions are generally in cream or lotion form. They are intended to moisturize, however, considerable loss of moisture results from evaporation during application or feathering of the composition within a short time after application.

There is thus a need for facial make-up compositions which impart moisture yet give a very smooth, silky, powder feel.

SUMMARY OF INVENTION

The invention is directed to a cosmetic compositions containing about 30.0-60.0% light oils, 1.0-10.0% cosmetic waxes, and 30-60% of a powder phase comprised of spherical silica, particulate nylon, and spherical powder, wherein the spherical component is 0.1-60% by weight of the total composition.

DETAILED DESCRIPTION

The cosmetic composition of the invention provides an excellent foundation-type make up. Prior to facial application the composition is a very soft, light, creme consistency. Upon application, the presence of a high spherical phase causes a rapid transition of the composition to an emollient silk powder finish.

The composition may also be used as a blush, lipstick, concealer, eyeshadow, moisturizer, sunscreen product, etc., upon the addition of the appropriate ingredients.

The composition of the invention contains five essential constituents. About 30.0-60.0% of light oils are found in the composition. Light oils mean oils of a low molecular weight such as dimethicone of less than 350 cs., octyl palmitate, isostearyl palmitate, PEG-4 diheptanoate, glycerol trioctanoate, isopropyl isostearate, octyl stearate, glycerol octanoate, neopentyl glycol diisooctanoate, or other oils of molecular weight in the same range as these oils. The light oils assist in solubilizing the cosmetic waxes which are an essential component of the invention. However, in the preferred embodiment of the invention dimethicone is used as the light oil. Since dimethicone is not soluble in cosmetic waxes, other light oils which are soluble in waxes are added to enhance the solubility of dimethicone in cosmetic waxes. In other words, mixtures of light oils are most effective, particularly if dimethicone is used.

Cosmetic waxes in approximately 1.0-10.0% range comprise the cosmetic wax portion of the composition. Cosmetic waxes means waxes traditionally used in cosmetic formulations for example, candelilla, microcrystalline wax, carnauba, beeswax, paraffin, spermaceti, petrolatum, glyceryl tribehenate, isostearyl behenate, etc.

The composition contains 30-60% of a powder phase comprised of spherical silica, particulate nylon and spherical powder wherein the spherical component is 0.1-60% of the total composition.

The term "spherical component" means the constituents of the powder phase which are spherical or nearly spherical in shape. As mentioned previously the desireable qualities of this cosmetic composition are due to the spherical phase. Thus the total composition of the invention must contain 0.1-60.0% of constituents which are spherical or nearly spherical in shape.

The term spherical silica means, in accordance with the invention, a silica of a particle size from 2-20 microns which is preferably spherical or nearly spherical in shape. Silica of this type and its Preparation are described in Japanese laid-open patent application No. 61-174103 which application is hereby incorporated by reference. It is known in the art to treat spherical substances in order to effect surface modifications which enhance the attributes of the material. The spherical silica of the invention may be treated with a variety of materials according to methods well known to those skilled in the art, such materials being lecithin, sodium hyaluronate, silicone, teflon, amino acids, sunscreens, isopropyltriisostearyl titanate, polymers such as polyethylene, titanium dioxide, or other suitable materials. The composition generally contains 0.1-15% by weight of the composition of spherical silica The composition also essentially contains particulate nylon. Particulate nylon or nylon, means nylon particles of an average particle size of less than 20 microns. Particulate nylon may be spherical or nearly spherical in shape. It is readily available from a number of commercial sources. The nylon may also be treated as described above. Generally the composition of the invention contains 0.1-20.0% by weight of the total composition of particulate nylon.

The cosmetic composition contains spherical powder as part of the powder Phase. Spherical powder means powder type materials which are spherical or nearly spherical in shape such as talc, mica, zinc stearate, acrylates copolymer, etc. These materials may be untreated or treated as set forth above. The total composition contains 0.1-60.0% by weight of the total composition of spherical powder.

It is necessary that the Powder Phase comprise about 30-60% of the total composition. The term "powder phase" means collectively spherical silica, particulate nylon, spherical powder, cosmetic coloring agents and spherical fillers. The total powder phase must equal 30-60% of the total composition and 0.1-60% by weight of the total cosmetic composition must be spherical.

In addition to the above constituents the cosmetic composition may contain cosmetic colors if color is desired, and spherical fillers. The cosmetic composition may also contain U.V. absorbers, wetting agents or preservatives. As mentioned Previously the powder Phase may include cosmetic coloring agents. The cosmetic coloring agents may be treated or untreated. Treated cosmetic coloring agents means organic or inorganic colors which are surface treated to add a certain benefit, change color or other characteristics such as decrease surface tension, increase adherence, or by adding certain other constituents as set forth above. These processes are well known to those skilled in the art. Inorganic pigments having various colors such as black, yellow and red iron oxides, ultramarine, chromium oxide, ferric ferrocyanide and so on are suitable. Suitable organic color pigments are all FDA approved D&C and FD&C colors. These colors are widely available from a number of commercial sources. Cosmetic coloring agents may comprise 0.1–45.0% by weight of the total composition.

The powder phase may also contain spherical fillers. Spherical fillers means materials which are spherical or nearly spherical in shape and function as fillers, for example titanium dioxide, zinc oxide, kaolin, magnesium oxide, magnesium carbonate, methylcellulose, other iron oxides, N-lauryl-L-lysine, etc. The spherical fillers may be untreated or treated as mentioned previously. Generally the composition contains 0.1–20.0% by weight of the total composition of spherical fillers.

The composition may optionally contain U.V. absorbers or sunscreens such as octylmethoxycinnamate, padimate O, benzophenones, PABA, and so on. About 0.5–10% of a U.V. absorber is suitable.

It may also be desireable to add one or more wetting agents which aid in pigment solubility. Suitable wetting agents are surfactants which have an HLB from 5–7, such as sorbitan trioleate, polyglycerol 3 diisostearate, sorbitan sesquioleate, and so on. About 0.1–1.5% of wetting agent is suitable.

Preservatives are desireable. The preservatives generally used in these types of compositions are suitable. For example the parabens such as methyl, ethyl, propyl or butyl paraben or mixtures thereof, phenoxyethanol, BHA, EDTA, etc. are appropriate. Suitable ranges may vary but generally 0.5–2% is appropriate.

The compositions of the invention can be Prepared by mixing together and Pulverizing all the dry ingredients, separately heating and blending the components of the oils and waxes. The dry ingredients are combined with the heated oils, waxes and emollients, and the mixture is stirred to achieve a uniform suspension of all ingredients. The composition is poured into its intended package and then cooled. Because of the carefully chosen ingredients these compositions are stable at temperatures encompassing 50° C.

As mentioned previously, the use of dimethicone in the composition of the invention makes the use of a mixture of light oils necessary since the cosmetic wax component is not soluble in dimethicone. In the preferred embodiment of the invention dimethicone is used thus necessitating a mixture of light oils in the composition. It is also preferable that the composition contain 0.1–45.0% treated cosmetic coloring agents and 0.1–20.0% spherical fillers.

In the preferred embodiment of the invention the preferred range of essential constituents is by weight of the total composition)

2.0–4.0% spherical silica
6.0–8.0% particulate nylon
8.0–25.0% spherical powder
43.0–46.0% light oils
6.0–8.0% cosmetic waxes In addition the Preferred embodiment also preferably contains 25.0–35.0% surface treated colors, and 13.0–15.0% spherical fillers, in addition to a U.V. absorber, wetting agent and Preservative. Of course, the Powder Phase is 30–60% by weight of the total composition and 0.1–60% by weight of the total composition is spherical. The Preferred spherical powder phase constituents are mica, Preferably mica treated with substances such as Polyethylene or dimethicone; and acrylates copolymer. The Preferred spherical fillers are talc, titanium dioxide and N-lauryl lysine. The preferred light oils are neopentylglycol diisooctanoate, dimethicone and octyl palmitate. The preferred cosmetic waxes are one or more of isostearyl behenate, glyceryl tribehenate, or candelilla wax. The preferred wetting agent is sorbitan trioleate, the preferred U.V. absorber is octylmethoxycinnamate, and the preferred preservatives BHA, and methyl/ethyl/propyl/butyl parabe in combination with phenoxyethanol. This preservative mixture is commercially available.

The invention will be further described in connection with the following examples which are set forth for the purposes of illustration only.

EXAMPLE 1

A concealer Cosmetic Composition was made by combining the following ingredients:

|  | W/W % |
| --- | --- |
| Isostearyl behenate | 3.00 |
| Glyceryl tribenehate | 3.50 |
| Candelilla wax | 0.40 |
| Octyl palmitate | 15.10 |
| Dimethicone | 25.00 |
| Neopentylglycol diisooctanoate | 5.60 |
| Sorbitan trioleate | 0.50 |
| Fragrance | 0.10 |
| Octylmethoxy cinnamate | 2.00 |
| BHA | 0.05 |
| [1]Methyl/ethyl/propyl/butyl/paraben and phenoxyethanol | 1.40 |
| Acrylates copolymer | 1.00 |
| Yellow iron oxide | 0.03 |
| Black iron oxide | 0.01 |
| Red iron oxide | 0.03 |
| [2]Mica, polyethylene, dimethicone | 10.00 |
| Titanium dioxide | 19.18 |
| Nylon | 7.00 |
| Talc | 0.05 |
| Spherical silica | 3.00 |
| N-lauryl L-lysine | 2.00 |
| [3]Mica, Bismuth oxychloride, titanium dioxide | 1.00 |

[1]available under tradename "Phenonip"
[2]mica coated with polyethylene and dimethicone
[3]mica coated with bismuth oxychloride and titanium dioxide

EXAMPLE 2

An eyeshadow was prepared using the cosmetic composition of the invention.

|  | W/W % |
| --- | --- |
| Isostearyl behenate | 3.00 |
| Glyceryl tribehenate | 3.50 |
| Candililla wax | 0.40 |
| Octyl palmitate | 15.10 |

-continued

| | W/W % |
|---|---|
| Dimethicone | 25.00 |
| Neopentyl glycol diisooctanoate | 5.60 |
| Sorbitan trioleate | 0.50 |
| Fragrance | 0.10 |
| Octylmethoxy cinnamate | 2.00 |
| Trisodium EDTA | 0.05 |
| BHA | 0.05 |
| Methyl/ethyl/propyl/butyl/paraben and phenoxyethanol | 1.40 |
| Acrylates copolymer | 1.00 |
| Ultramarine blue | 0.90 |
| Yellow iron oxide | 0.20 |
| Black iron oxide | 0.05 |
| Red iron oxide | 0.20 |
| Mica, polyethylene, dimethicone | 10.00 |
| Titanium dioxide | 11.00 |
| Nylon | 7.00 |
| Talc | 6.95 |
| Spherical silica | 3.00 |
| N-lauryl L-lysine | 2.00 |
| Mica, Bismuthoxychloride, Titanium dioxide | 1.00 |

EXAMPLE 3

The cosmetic composition of the invention was used to prepare a foundation:

| | W/W % |
|---|---|
| Isostearyl behenate | 3.00 |
| Glyceryl tribehenate | 3.50 |
| Candelilla wax | 0.40 |
| Octyl palmitate | 15.10 |
| Dimethicone | 25.00 |
| Neopentyl Glycol diisooctanoate | 5.60 |
| Sorbitan trioleate | 0.50 |
| Fragrance | 0.10 |
| Octyl methoxy cinnamate | 2.00 |
| Trisodium EDTA | 0.05 |
| BHA | 0.05 |
| Methyl/ethyl/propyl/butyl/paraben and phenoxyethanol | 1.40 |
| Acrylates copolymer | 1.00 |
| Yellow iron oxide | 1.93 |
| Black iron oxide | 0.26 |
| Red iron oxide | 0.73 |
| Mica, polyethylene, dimethicone | 10.00 |
| Titanium dioxide | 11.00 |
| Nylon | 7.00 |
| Talc | 5.38 |
| Spherical silica | 3.00 |
| N-lauryl L-lysine | 2.00 |
| Mica, Bismuth oxychloride, Titanium dioxide | 1.00 |

EXAMPLE 4

The cosmetic composition of the invention was used to prepare a moisturizer as set forth below:

| | W/W % |
|---|---|
| Isostearyl behenate | 3.00 |
| Glyceryl tribehenate | 3.50 |
| Candelilla wax | 0.40 |
| Octyl palmitate | 15.10 |
| Dimethicone | 25.00 |
| Neopentyl Glycol diisooctanoate | 5.60 |
| Sorbitan trioleate | 0.50 |
| Fragrance | 0.10 |
| Octyl methoxy cinnamate | 2.00 |
| Trisodium EDTA | 0.05 |
| BHA | 0.05 |
| Methyl/ethyl/propyl/butyl/paraben & phenoxyethanol | 1.40 |

-continued

| | W/W % |
|---|---|
| Acrylates copolymer | 1.00 |
| Mica, polyethylene, dimethicone | 13.92 |
| Nylon | 7.00 |
| Talc | 5.38 |
| Spherical silica | 3.00 |
| N-lauryl L-lysine | 2.00 |
| Mica, bismuth oxychloride, titanium dioxide | 1.00 |

EXAMPLE 5

The cosmetic composition of the invention was used to prepare a blush.

| | W/W % |
|---|---|
| Isostearyl behenate | 3.50 |
| Glyceryl tribehenate | 4.00 |
| Candelilla wax | 0.50 |
| Octyl palmitate | 15.50 |
| Dimethicone | 26.00 |
| Neopentyl glycol diisooctandate | 5.00 |
| Sorbitan trioleate | 0.50 |
| Fragrance | 0.10 |
| Trisodium EDTA | 0.05 |
| BHA | 0.05 |
| Methyl/ethyl/propyl/butyl/paraben and phenoxyethanol | 1.40 |
| Acrylates copolymer | 1.00 |
| Red iron oxide | 0.67 |
| Mica, polyethylene, dimethicone | 10.00 |
| Titanium dioxide | 10.00 |
| Nylon | 7.00 |
| Talc | 9.60 |
| Spherical silica | 2.50 |
| N-lauryl L-lysine | 2.00 |
| FD&C yellow #5 | 0.18 |
| D&C red #7 | 0.45 |

EXAMPLE 6

The cosmetic composition of the invention was used to make a lipstick.

| | W/W % |
|---|---|
| Isostearyl behenate | 3.00 |
| Glyceryl tribehenate | 3.50 |
| Candelilla wax | 0.40 |
| Octyl palmitate | 15.10 |
| Dimethicone | 25.00 |
| Neopentyl Glycol diisooctanoate | 5.60 |
| Sorbitan trioleate | 0.50 |
| Fragrance | 0.10 |
| Octylmethoxy cinnamate | 2.00 |
| Trisodium EDTA | 0.05 |
| BHA | 0.05 |
| Methyl/ethyl/propyl/butyl/paraben and phenoxyethanol | 1.40 |
| Acrylates copolymer | 1.00 |
| D&C Red #7 | 5.00 |
| D&C Red #30 | 0.50 |
| D&C Yellow #10 | 0.50 |
| Mica, polyethylene, dimethicone | 10.00 |
| Titanium dioxide | 5.00 |
| Nylon | 7.00 |
| Talc | 8.30 |
| Spherical silica | 3.00 |
| N-lauryl L-lysine | 2.00 |
| Mica, Bismuth oxychloride, Titanium dioxide | 1.00 |

While the invention has been described in connection with the preferred embodiment it is not intended to limit the scope of the invention to the particular form set forth but on the contrary it is intended to cover such alternatives, modification, and equivalents as may be included within the spirit and scope of the invention as defined by the appended claims.

We claim:

1. A cosmetic make-up composition consisting essentially of 30.0–60.0% light oils selected from the group consisting of dimethicone of less than 350 c.s., oclyl palmitate, isostearyl palmitate, PEG-4 ditceptanoate, glycerol trioctanoate, isopropyl isostearate, octyl stearate, glycerol octanoate, neopentyl glycol diisooctanoate, or mixtures thereof, 1–10% cosmetic waxes, 0.1–15% spherical silica particles of 2–20 microns in diameter, 0.1–20% nylon particles of less than 20 microns in diameter, 8–25% spherical powder particles selected from the group consisting of talc, mica, zinc stearate, acrylates copolymer, or mixtures thereof, and 13–15% spherical fillers selected from the group consisting of titanium dioxide, zinc oxide, kaolin, magnesium oxide, magnesium carbonate, methyl cellulose, iron oxides, N-lauryl-1-lysine, or mixtures thereof, a colorant, UV absorber, wetting agent, preservative, fragrance, or mixtures thereof.

2. The composition of claim 1 wherein the cosmetic waxes are selected from the group consisting of isostearyl behenate, glyceryl tribehenate, candelilla wax, microcrystalline wax, carnauba, beeswax, paraffin, spermaceti, petrolatum, or mixtures thereof.

3. The composition of claim 1 wherein the colorant is present at 0.1–45%, the UV absorber is present at 0.5–10%, the wetting agent is present at 0.1–1.5%, and the preservative is present at 0.5–2%.

* * * * *